(12) United States Patent
Quine et al.

(10) Patent No.: US 7,340,970 B2
(45) Date of Patent: Mar. 11, 2008

(54) METHOD AND DEVICE FOR ISOLATING, COLLECTING AND TRANSFERRING HAZARDOUS SAMPLES

(75) Inventors: Douglas B. Quine, Bethel, CT (US); Denis J. Stemmle, Stratford, CT (US); John E. Massucci, Eastchester, NY (US); Deborra J. Zukowski, Newtown, CT (US)

(73) Assignee: Pitney Bowes Inc., Stamford, CT (US)

( * ) Notice: Subject to any disclaimer, the term of this patent is extended or adjusted under 35 U.S.C. 154(b) by 836 days.

(21) Appl. No.: 10/742,476

(22) Filed: Dec. 19, 2003

(65) Prior Publication Data

US 2005/0136540 A1 Jun. 23, 2005

(51) Int. Cl.
*G01N 1/24* (2006.01)
(52) U.S. Cl. .................. 73/864.74; 73/31.03
(58) Field of Classification Search ............. 73/864.74, 73/31.03
See application file for complete search history.

(56) References Cited

U.S. PATENT DOCUMENTS

| 4,069,965 | A | 1/1978 | Maddox, Jr. ................. 232/19 |
| 4,461,184 | A | 7/1984 | Gandhi et al. |
| 5,099,679 | A | 3/1992 | Huerlimann et al. ....... 73/19.06 |
| 5,368,226 | A | 11/1994 | Franceschino ............... 232/19 |
| 5,429,803 | A | 7/1995 | Guirguis ...................... 422/58 |
| 6,324,927 | B1 | 12/2001 | Ornath et al. ............. 73/864.33 |
| 6,463,815 | B1 | 10/2002 | Tallentire ................. 73/863.23 |
| 6,740,836 | B2 | 5/2004 | Ryan ........................... 209/584 |
| 6,742,703 | B2 | 6/2004 | Esakov ......................... 232/45 |
| 6,789,727 | B2 | 9/2004 | Felice .......................... 232/44 |
| 2003/0074987 | A1 | 4/2003 | Dalmia et al. ................ 73/864 |
| 2003/0136179 | A1* | 7/2003 | Felice et al. ............... 73/31.03 |
| 2003/0155412 | A1 | 8/2003 | Felice .......................... 232/45 |
| 2003/0209595 | A1 | 11/2003 | Felice |
| 2004/0027036 | A1* | 2/2004 | Hall .............................. 312/1 |
| 2004/0045342 | A1* | 3/2004 | Jones et al. ................... 73/37 |
| 2005/0008533 | A1 | 1/2005 | Avant .......................... 422/28 |

FOREIGN PATENT DOCUMENTS

| EP | 0429396 B1 | 5/1991 |
| EP | 1366696 A2 | 3/2003 |
| GB | 1067166 | 5/1967 |
| GB | 2303111 A | 2/1997 |
| WO | 03/054778 A1 | 7/2003 |
| WO | 03/058207 A2 | 7/2003 |

* cited by examiner

*Primary Examiner*—Hezron Williams
*Assistant Examiner*—Paul M West
(74) *Attorney, Agent, or Firm*—George M. Macdonald; Angelo N. Chaclas

(57) ABSTRACT

A method and system for isolating, transferring and testing potentially contaminated mail pieces. The mail pieces are encapsulated in a sealed package at one location and transferred to another location for testing. During testing, the sealed package is connected to an air sampling system, which directly draws an air sample from the sealed package. At the end of testing, the air pressure in the sealed package is sufficiently reduced, causing the sealed bag to collapse. A septum or a tube with a self-sealed coupler is provided on the sealed package to allow the air sampling system to draw air out of the sealed package. When the air sampling system is not connected to the sealed package, the septum or the self-sealed coupler prevents the air inside the sealed package from escaping into the environment. It is advantageous to disturb the mail pieces during air sampling.

26 Claims, 8 Drawing Sheets

METHOD AND DEVICE FOR ISOLATING, COLLECTING AND TRANSFERRING HAZARDOUS SAMPLES

CROSS REFERENCES

The present application is related to commonly owned, co-pending U.S. Patent Application entitled "Method And System For Isolating And Testing Biological Contaminants In Mail Packages" Ser. No. 10/742,106 in the names of Douglas B. Quine and Denis J. Stemmle, which is hereby incorporated by reference.

The present application is related to commonly owned, co-pending U.S. Patent Application entitled "Method And Device For Collecting And Transferring Biohazard Samples" Ser. No. 10/741,264 in the names of Douglas B. Quine, Ashwani Sharma, and John E. Massucci which is hereby incorporated by reference.

FIELD OF THE INVENTION

The present invention relates generally to biohazard detection and, more particularly, to the isolation, collection and transferring of a biohazard sample trapped in a filter of a detection system.

BACKGROUND OF THE INVENTION

In late 2001, several United States postal offices and other buildings were contaminated with *Bacillus anthracis* spores (anthrax) along the eastern United States, resulting in anthrax infection and death among several individuals. This incident was quite costly, not only in terms of the health-related impact, but also in the required decontamination efforts. Cleanup following the anthrax contamination proved to be difficult, labor intensive, and expensive. As this threat still exists, there is a need to detect biological contaminants within the postal packages or other containers. Similar attacks through the mail system are possible using other hazardous substances such as nerve or blistering agents, or any other substance which can harm any person who handles the contaminated mail piece.

Detection of biohazards in the mail for culture or polymerase chain reaction (PCR) analysis requires collection of a sample. Similar detection technologies for other harmful contaminants also require collection of samples. Currently, when mail is suspected of carrying biological contaminants such as anthrax, the mail is put in a bag and carried to a testing facility. At the testing facility, the bag is opened in a chemical hood, and the mail is taken out of the bag. A wet cotton swab or the like is used to take a sample of the suspected contaminants from the mail for testing. Wet cotton swabs may cause damage to the forensic evidence by matting dry powders or causing ink to run. The mail is then bagged for safekeeping or further processing. As such, part of the suspected contaminants will be lost in the chemical hood and contaminate the equipment disposed therein. Furthermore, the mail is required to be bagged more than once.

Thus, it is advantageous and desirable to provide a safer method and system for containing the mail and collecting the suspected biological contaminants on the mail.

SUMMARY OF THE INVENTION

The present invention provides a method and system for isolating, transferring and testing particles that may be biological or other hazardous contaminants carried by a mail piece or a mail tray.

The mail pieces, along with the mail tray, are encapsulated in a sealed package at one location and transferred to another location for testing so as to minimize the contamination at the testing location and any other location through which the mail passes. The sealed package is connected to an air sampling system, which directly draws an air sample from the sealed package through a filter chamber so that particles suspected to be biological or other hazardous contaminants are trapped on a filter in the filter chamber. The container that is used to encapsulate the mail pieces may be transparent so as to allow visual inspection of the sealed package. The container may be flexible so that it may collapse during or at the end the sample collection process. A tube with a self-sealed coupler is provided on the sealed package to allow the air sampling system to draw air out of the sealed package. When the air sampling system is not connected to the sealed package, the self-sealed coupler prevents the air inside the sealed package from escaping into the environment. The mail pieces and the mail tray in the sealed packages are manually or mechanically disturbed before or during air sampling so as to dislodge the particles carried by the mail pieces or the mail tray.

The present invention will become apparent upon reading the description taken in conjunction with FIGS. 1 to 9.

DETAILED DESCRIPTION OF THE INVENTION

Figure 1:
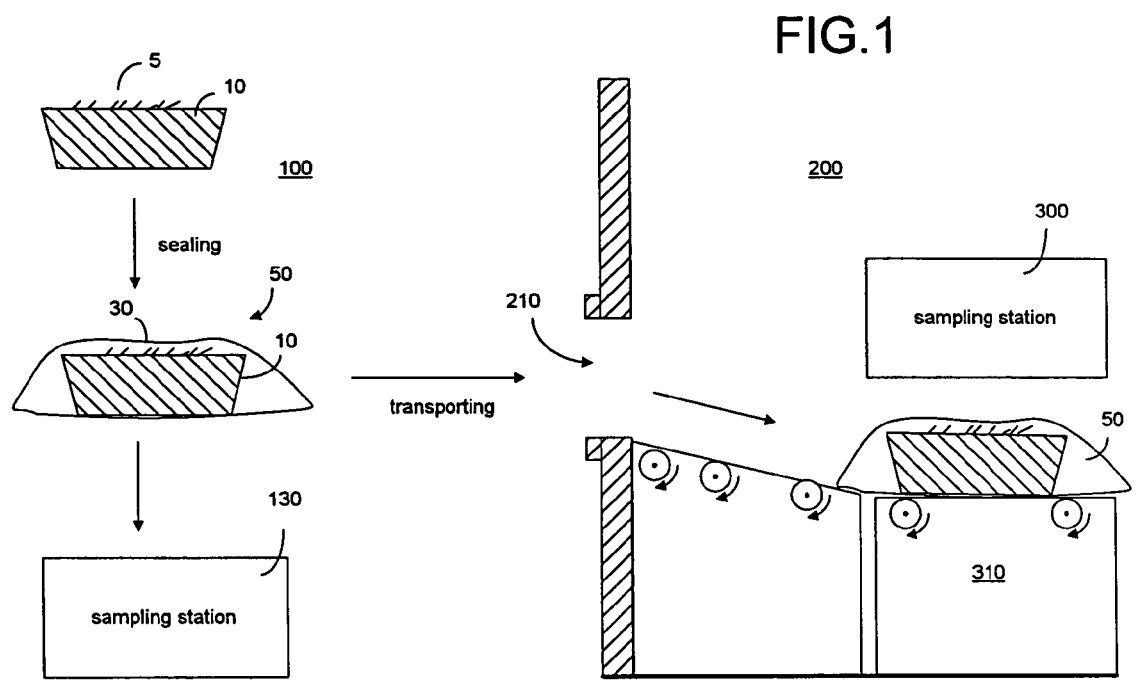
FIG. 1 is a schematic representation illustrating the method and system for isolating and transferring suspected contaminated samples, according to the present invention.

The present invention uses a dry filter collection assembly to collect the suspected biological or other hazardous contaminants from a sealed container containing one or more mail pieces. According to the present invention, the container is sealed at one location and the suspected biological contaminants are tested at the same location or at another location. As shown in FIG. 1, a mail-tray 10 containing mail pieces 5 that may be contaminated with biological or other hazardous contaminants is encapsulated in a flexible bag 30 at a location 100. The sealed package 50 may then be transported to a different location 200 for testing. For example, location 200 can be a building that has a window 210 to accept the sealed package 50. Through a conveyor belt or the like, the sealed package 50 is transferred to a jogger 310 in a collecting station 300. The sealed package 50 may contain air or a gas, such as nitrogen. In order to reduce the possibility that the biological or other hazardous contaminants will contaminate the outside of the bag 30, it is possible to clean the outside of the bag 30 with an appropriate cleaning agent, or to put the mail tray 10 in a double nested bag. Prior to transferring the mail tray into the building, the outer bag can be removed and properly discarded. Alternatively, once the mail is put in the sealed container at location 100, it may be transported by any means for any distance to testing location 200 without risking contamination of facilities or personnel along the route of transit.

Figure 2:
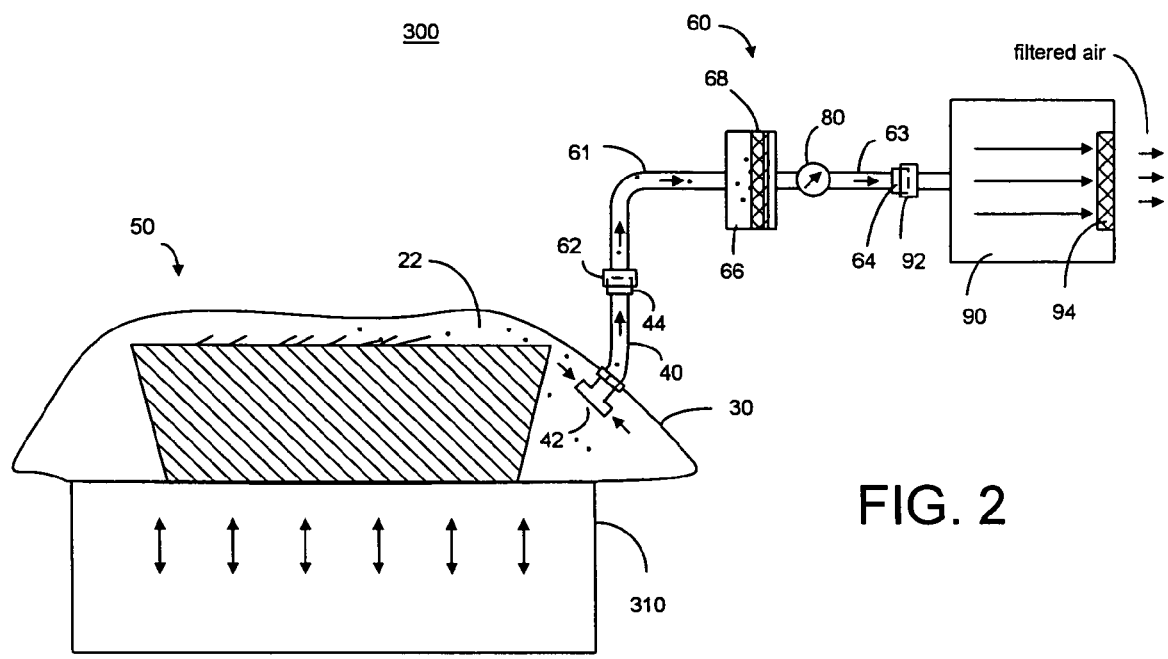
FIG. 2 is a schematic representation illustrating the method and system for collecting suspected contaminated samples, according to the present invention.

As shown in FIG. 2, the sealed package 50 has a tube 40 to allow a sample collection system 60 to collect the suspected hazardous contaminants from the sealed package 50. One end of the tube 40 has an open inlet 42, which is shaped like a "T" or has a number of orifices so that there are multiple sub-inlets to prevent blockage of air flow in the event that the end of the inlet touches the inner walls of the bag 30. The other end of the tube 40 has coupler 44. The air sample collection system 60 comprises a filter chamber 66 having an air filter 68. The filter can be wet or dry. One end of the filter chamber 66 is connected to a first air passageway 61, which is securely affixed to a coupler 62. The other end of the filter chamber 66 is connected to a second air passageway 63, which is securely affixed to a coupler 64. The coupler 62 is different from the coupler 64. For example, only the coupler 62 on the filter chamber 66 can be operatively engaged with the coupler 44 on the tube 40. The coupler 64 is operatively connected to an air pump 90 through a coupler 92 so as to allow air to be drawn out of the interior 22 of the bag 30 through the filter chamber 66. It is important that the couplers 44, 62, 64 and 92 are self-sealed such that each of the couplers is closed when it is not engaged with another coupler. It should be noted that the pores on the filter 68 should be small enough to trap suspected contaminants. For example, the filter 68 is a HEPA filter. In order to reduce or eliminate the possibility that the suspected hazardous contaminants contaminate the surrounding, it is advantageous to use another fine air filter 94, such as HEPA, in the air pump 90. Prior to or during the sample collection process, it is advantageous to disturb the mail pieces in the sealed package 50 so as to cause the suspected contaminants attached to the mail pieces or the mail tray to be dislodged and aerosolized. For example, the mail pieces in the sealed package 50 can be manually disturbed or disturbed by the vibration of the jogger 310. It is advantageous to install a flow gauge 80 in the air passageway 63 to provide visual confirmation that the air passageways 61, 63, the tube 40 or the air inlet 42 is not blocked. It is possible that the air pump 90 provides an audible change in pitch and volume when the airflow is impeded. Such pitch or sound volume change warns the operator to look for problems.

Figure 8:
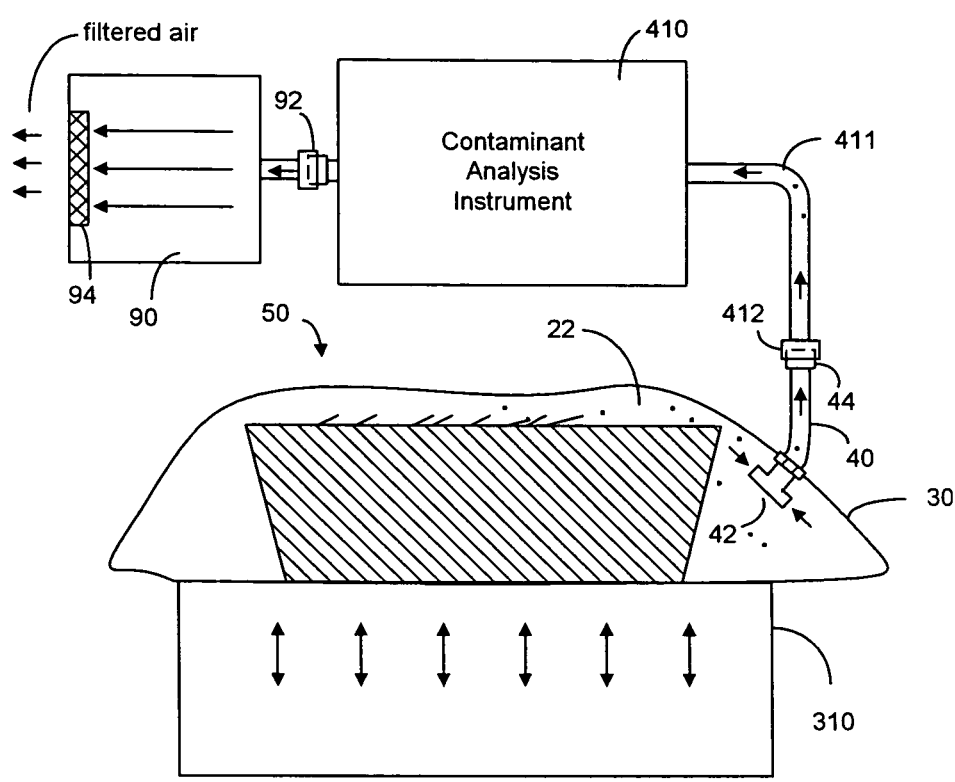
FIG. 8 is a schematic representation illustrating the method and system of testing suspected contaminated samples directly from a sealed container.

Alternately, an instrument for direct analysis of the air stream and any particles suspended in it may be substituted for or combined with the air sample collection system 60 comprising filter chamber 66 having an air filter 68, as shown in FIG. 8.

Figure 3:
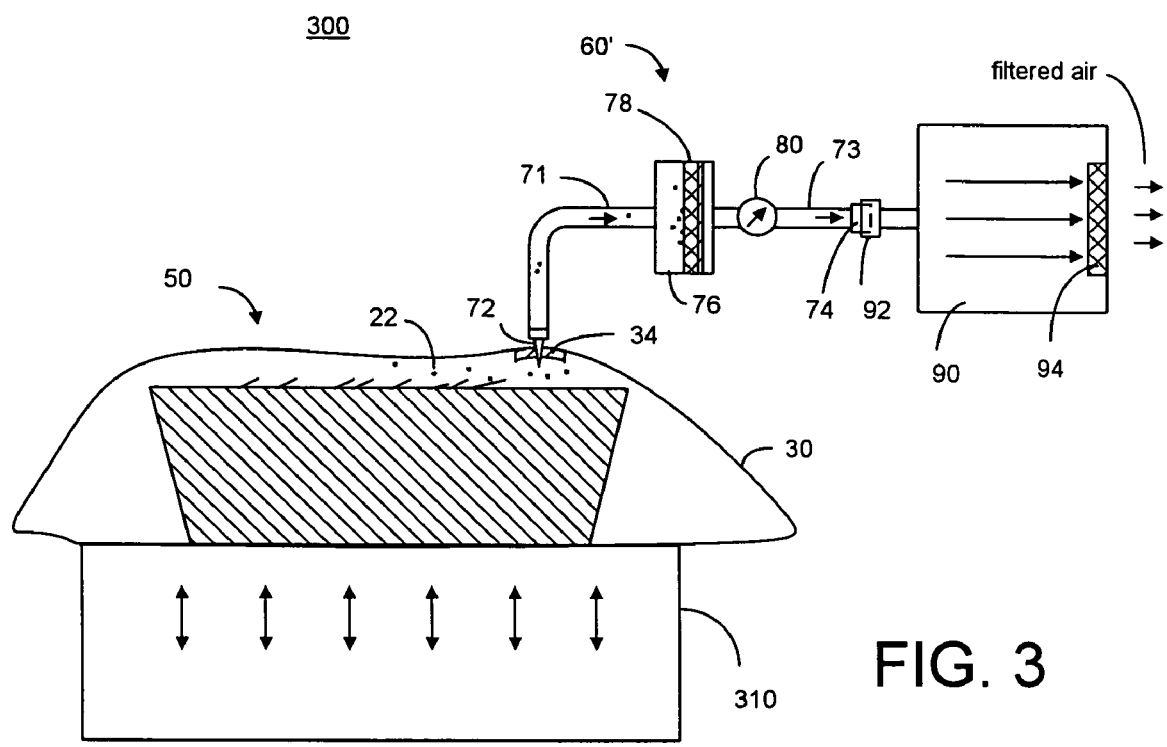
FIG. 3 is a schematic representation illustrating another method and system for collecting suspected contaminated samples, according to the present invention.

Alternatively, instead of having a tube 40 on the bag 30 to allow air within the sealed package 50 to be drawn out for testing, it is possible to put a septum 34 on the bag 30, as shown in FIG. 3. Instead of using a filter chamber 66 that has a coupler 62, it is possible to use a filter chamber 76 that has a needle 72 for reaching into the interior 22 of the sealed package 50 through the septum 34. As with the filter chamber 66, the filter chamber 76 also has an air filter 78 to trap the suspected contaminants. The filter chamber 76 also has a first air passageway 71 on one end and a second passageway 73 on the other end. The second passage way 73 is securely affixed to a self-sealed coupler 74, which can be operatively engaged with the coupler 92 of the air pump 90.

It is advantageous to have a clear filter chamber 66 or 76 to allow visual confirmation of the replacement of filter 68 or 78 within the filter chamber.

Figure 4A:
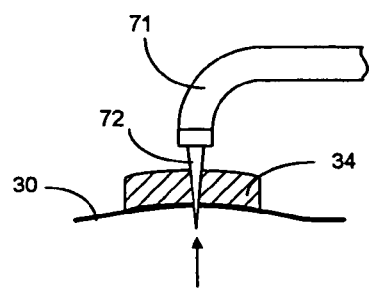
FIG. 4a is a schematic representation illustrating a septum on the sealed package being engaged with a sample collecting tube.
Figure 5A:
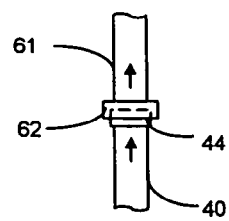
FIG. 5a is a schematic representation illustrating a tube extended from the sealed package being engaged with the sample collecting tube.
Figure 4B:
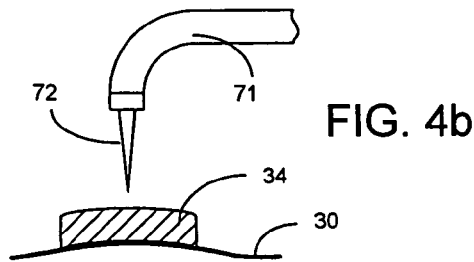
FIG. 4b is a schematic representation illustrating the septum on the sealed package being disengaged from the sample collecting tube.
Figure 5B:
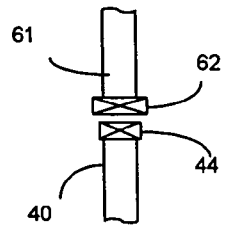
FIG. 5b is a schematic representation illustrating the tube from the sealed container being disengaged from the sample collecting tube.
Figure 6A:
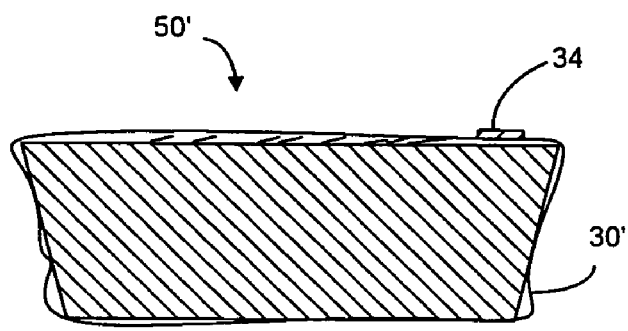
FIG. 6a is a schematic representation illustrating a collapsed, sealed container having a septum disposed thereon.
Figure 6B:
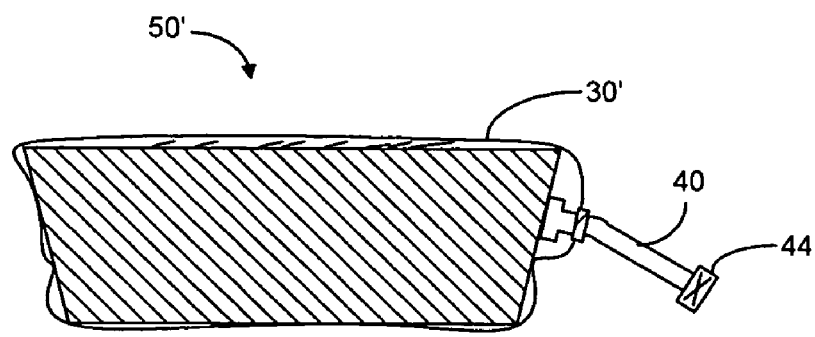
FIG. 6b is a schematic representation illustrating a collapsed, sealed container having a tube extended therefrom.

It should be noted that the septum 34 is a self-sealed material such that it allows the needle 72 to reach into the bag 30 to draw an air sample therefrom, as shown in FIG. 4a. But when the needle 72 is pulled off from the septum 34, the septum 34 is effectively closed off to prevent air inside the bag 30 from leaking out, as shown in FIG. 4b. Likewise, the couplers 62 and 44 are also self-sealed. When the coupler 44 and coupler 62 are operatively engaged with each other, air is allowed to be drawn into the passageway 61 via the tube 40 and the couplers 44 and 62, as shown in FIG. 5a. When the coupler 44 and coupler 62 are disengaged from each other, each of the couples 44 and 62 is closed (marked with an "X"), as shown in FIG. 5b.

Advantageously, the bag 30 is made of a soft and flexible material and the air pressure in the sealed package 50 is close to ambient pressure during sampling. When air is removed from the sealed package 50 during the collection procedure, the bag 30 will collapse and the air pressure inside the collapsed package 50' is lower than ambient. As such, any leaks or improper seals will cause air leakage into the bag 30, not venting into the environment. Furthermore, the collapsed sealed package 50' is less likely to be accidentally punctured. Due to the self-sealing nature of the septum 34 and the coupler 44, air exchange between the exterior and interior of the sealed package 50' is prevented.

It will be evident to anyone skilled in the art, that numerous alternate types of containers can similarly be used advantageously within the system described above. One alternative container is a sealable box having flexible sides. When sample air is withdrawn from the box, the sides flex and a lower than ambient air pressure occurs inside the sealed container. Another alternative is a rigid box which further includes a one way air inlet valve which allows air to enter as the sample is being withdrawn.

It is advantageous that the container material is anti-static so that the suspected biohazard particles in the container, once aerosolized, stay in the air instead of becoming attached to the surface of the container. In another embodiment, the items to be tested occupy less than half the volume of the sealed package so as to allow a relatively large volume of air for sample collection and testing. Such sample collection is made at six liters per minute without significant backpressure. A majority of the extra open air space is preferably located above the open container that holds the items to be tested, but could be located on the side of the sealed package.

It should be appreciated that taking an air sample from a sealed package 50 only through the tube 40 or the septum 34 will allow some of the remaining suspected hazardous material to remain within the sealed package. If it is necessary to take additional or extended samples, it is possible to introduce air into the collapsed sealed package through the tube 40 or the septum 34. After connecting the air sampling system 60 to this re-inflated sealed package, the mail pieces in the sealed package can be disturbed again in order to increase the concentration of the suspected hazardous particles in the air. In contrast, if a sealed package is opened in a safety chemical hood in order to collect a sample of the contaminants, substantial amount of the suspected hazardous particles may be lost in the air. As such, the concentration of the suspected contaminants on the mail pieces or in the bag will be reduced.

Figure 7:
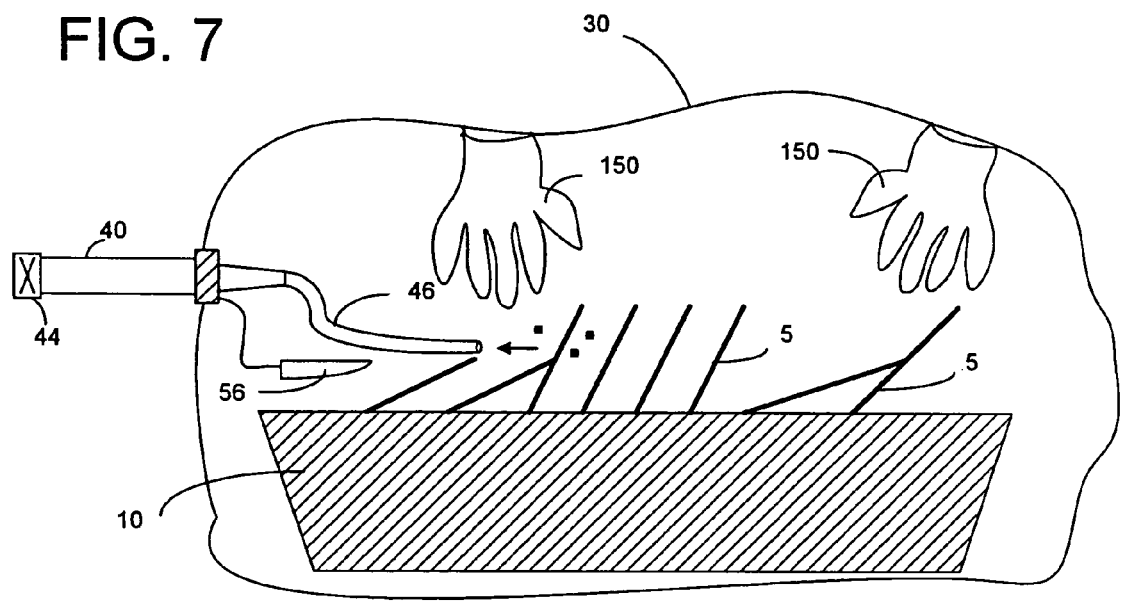
FIG. 7 is a schematic representation illustrating a glove bag used as a container for encapsulating mail pieces in a mail tray.

In order to increase the efficiency of contaminant collection, it is possible to use a glove bag as shown in FIG. 7. As shown, the bag 30' has one or two gloves 150 to allow an operator to access the mail pieces 5 inside the bag 30' through the gloves. A collection probe 46, which is securely attached to the tube 40, can be inserted into an envelope or mail piece to directly collect air and powder samples from inside the envelope. A sharp edge 56 can be provided inside the sealed package so that it can be used to make a short slit on an envelope or mail piece to ensure that there is no inner seal containing a biological hazard. A short slit allows the collection probe 46 to be inserted into the envelope without comprising the privacy of the contents.

It should be noted that the sample collection system as depicted in FIGS. 2 and 3 can be powered by a portable power source or by a wall outlet. It is possible to collect the air samples at the sealing location, inside a customer building or at a laboratory test location. The encapsulation of the mail pieces not only prevents the contaminants from contaminating the surrounding, but also preserves the evidence of the mail being contaminated. The encapsulation provides safety to the employees and the building. It also maximizes the ability to collect the hazard sample. Collecting the samples directly from the sealed package minimizes the lost of evidence. In contrast, opening a mail piece in a chemical hood and obtaining a sample in the chemical hood may cause some powder or particles to come out of the mail piece and be vacuumed away, thereby losing evidence.

It will also be noted that the system described has additional benefit for the mail handlers. Typically, mail is delivered to a mail-receiving establishment stacked in one or more standard mail trays. It is well known that any hazardous materials inside mail pieces can easily move to the outside of the mail pieces and become aerosolized when individual mail pieces are handled either manually or using automated equipment. Such inadvertent aerosolization creates a hazard for the mail handler and all other people in the vicinity. It further contaminates the environment, requiring personnel to abandon the facility, and expensive processes used to clean the environment. It is desirable to limit the possibility of such contamination of the mail handlers and the environment even at the initial arrival location 100. For this reason, it is a further advantage of this invention to enable the mail handler to handle only the mail tray without the need to handle the individual mail pieces. This reduces the possibility of inadvertent contamination of the environment.

It is a further benefit of this invention that the mail remains in the original tray, and the mail and the tray remain sealed inside the container until the tests are completed to determine if hazardous materials are present. When the mail in the tray is determined by test to not be contaminated with hazardous substances, the tray and the mail can be removed from the container—and processed in the normal fashion without requiring any further additional steps.

Figure 9:
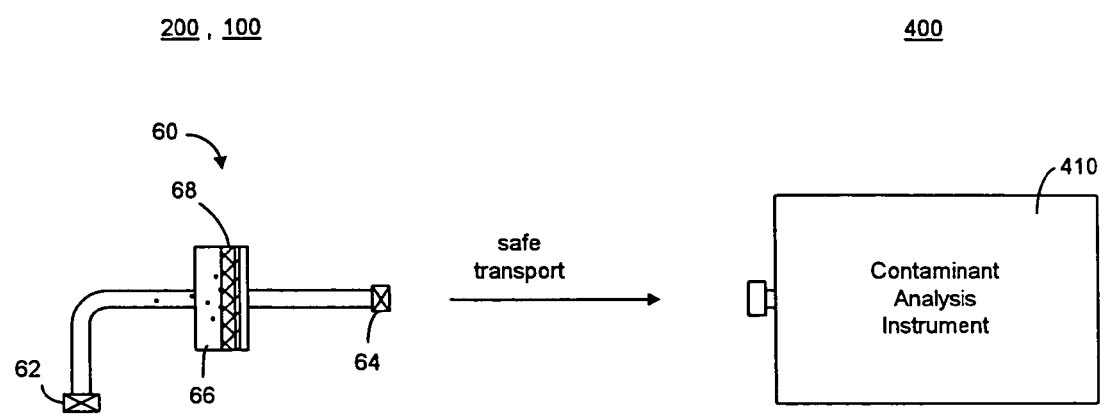
FIG. 9 is a schematic representation illustrating a filter chamber being safely transported to a remote location for testing the possible contaminants trapped in the filter chamber.

It should be noted that FIGS. 2 and 3 illustrate how the suspected contaminants are collected using a filter chamber 66 or 76 to trap the particles in the air within the sealed package 30. The trapped particles on the filter 68 or 78 must be further tested to determine whether those particles are indeed contaminants. For example, the filter chamber 66 can be safely transported from the collecting location 200 or 100 to a remote location 400 for testing, using a contaminant analysis instrument 410, such as a PCR analysis machine or other suitable instrument, as shown in FIG. 9. However, it is also possible to install a contaminant analysis instrument at the sealing location 100 or the sample collection location 200. As shown in FIG. 8, the contaminant analysis instrument 410 is operatively connected to a sealed package 30 to detect the contaminants directly. As shown, the analysis instrument 410 is connected to the sealed package 30 via an air passage 411 and a seal-sealed coupler 412. The analysis instrument 410 is also connected to an air pump 90, which draws an air and particle samples from the sealed package 30 through the analysis instrument.

Although the invention has been described with respect to a preferred embodiment thereof, it will be understood by those skilled in the art that the foregoing and various other changes, omissions and deviations in the form and detail thereof may be made without departing from the scope of this invention.

What is claimed is:

1. A method of testing items carrying particles that may be contaminants, comprising:

sealing the items in a package containing a gas; and checking for the contaminants while keeping the package substantially sealed, wherein said checking comprises collecting a gas sample from the package through a filter for trapping on the filter at least part of the particles in the gas sample;

wherein the filter is disposed in a filter chamber having a first air passageway and a second air passageway, the first passageway operatively connected to a gas outlet on the package, the second passageway operatively connected to an air pump to draw the gas sample from the outlet through the first passageway, the filter chamber and the second passageway; and wherein the package comprises a self-sealable member disposed thereon, and the first passageway is securely connected to a needle for piercing the self-sealable member in order to provide the gas outlet.

2. The method of claim 1, wherein the package is made of a flexible material so that the package becomes substantially collapsed during said collecting.

3. The method of claim 2, wherein the self-sealable member substantially prevents air from leaking into the collapsed package so as to keep the collapsed package substantially the same after said collecting.

4. A method of testing items carrying particles that may be contaminants, comprising:

sealing the items in a package containing a gas; and checking for the contaminants while keeping the package substantially sealed, wherein said checking comprises collecting a gas sample from the package through a filter for trapping on the filter at least part of the particles in the gas sample; wherein the filter is disposed in a filter chamber having a first air passageway and a second air passageway, the first passageway operatively connected to a gas outlet on the package, the second passageway operatively connected to an air pump to draw the gas sample from the outlet through the first passageway, the filter chamber and the second passageway; and wherein the package comprises a tube having a first end extended into the package and a second end connected to a self-sealable coupler, and wherein the first passageway is securely connected to a further coupler, so as to provide the gas outlet by engaging the further coupler to the self-sealable coupler.

5. The method of claim 4, wherein said sealing is carried at one location and said checking is carried out at another location.

6. The method of claim 4, wherein said sealing and checking is carried out at substantially the same location.

7. The method of claim 4, wherein said collecting is carried out at one location, further comprising transferring the filter chamber to another location for determining the contaminants from the particles trapped on the filter.

8. The method of claim 4, wherein the first end of the tube is inserted into at least one of the items for collecting the gas sample from said one of the items.

9. The method of claim 8, wherein the package contains a cutting member inside the package for opening a part of said one of the items, so as to allow the first end of the tube to be inserted into the opening for said collecting.

10. The method of claim 4, wherein the further coupler is also self-sealable.

11. The method of claim 4, wherein the package is made of a clear material, said checking comprising visually inspecting an inner surface of the package.

12. The method of claim 4, wherein the package is made of an anti-static material so as to reduce the amount of the particles sticking on the package.

13. The method of claim 4, further comprising agitating the items to cause at least part of the particles carried in the items to move into the gas in the package.

14. The method of claim 4, wherein the items comprise mail pieces.

15. The method of claim 4, wherein, said sealing further includes sealing a container containing the items in the package containing the gas; and the items occupy less than half the volume of the sealed package.

16. The method of claim 4, further comprising retaining the items in the sealed package until after results of said checking step are complete.

17. The method of claim 4, wherein the items in the package are contained in a tray, said method further comprising agitating the items along with the tray to cause at least part of the particles carried by the items or the tray to move into the gas in the package.

18. The method of claim 4, wherein the gas comprises air.

19. The method of claim 4, wherein the package is made of a flexible material so that the package becomes substantially collapsed during said collecting.

20. The method of claim 19, wherein the self-sealable coupler substantially prevents air from leaking into the collapsed package so as to keep the collapsed package substantially the same after said collecting.

21. A system for testing items carrying particles that may be contaminants, wherein the items are sealed in a container containing a gas, the container having a self-sealable air outlet, said system comprising:

a gas drawing device;

a device for operating on the gas drawn, and a first air passageway and a second air passageway, wherein the first passageway is operatively connected to the gas drawing device, and a second air passageway connected to the air outlet so as to draw an gas sample from the sealed container through the air outlet, the first passageway and the device for operating on the drawn gas;

wherein the container is a bag made of a flexible material so that the sealed container becomes substantially collapsed when the air pump draws the gas sample from the sealed bag.

22. The system of claim 21, wherein the device for operating on the gas drawn comprises a filter chamber having an air filter.

23. The system of claim 21, wherein the device for operating on the gas drawn comprises an instrument for analyzing at least one of the gas and any particles suspended in the gas.

24. The system of claim 21, wherein the items comprise mail pieces.

25. The system of claim 21, further comprising a mechanism, disposed in relation to the sealed container, for agitating the items while the gas is being drawn.

26. The system of claim 21, wherein the items are contained by a further container, said further container being sealed in the container along with the items.

* * * * *